United States Patent [19]

Fildes et al.

[11] 4,235,988

[45] Nov. 25, 1980

[54] DELIVERY MEANS FOR BIOLOGICALLY ACTIVE AGENTS

[75] Inventors: Francis J. T. Fildes; Francis G. Hutchinson, both of Macclesfield, England

[73] Assignee: Imperial Chemical Industries Limited, London, England

[21] Appl. No.: 44,213

[22] Filed: May 31, 1979

Related U.S. Application Data

[63] Continuation-in-part of Ser. No. 855,332, Nov. 28, 1977, Pat. No. 4,202,880.

[30] Foreign Application Priority Data

Dec. 13, 1976 [GB] United Kingdom ............... 51917/76
Nov. 30, 1977 [AU] Australia ........................... 31065/77
Nov. 30, 1977 [PK] Pakistan ............................. 436/77

[51] Int. Cl.³ ...................... C08G 18/48; A61K 9/02; A61K 31/557; A61K 31/785

[52] U.S. Cl. ........................................ 528/79; 128/285; 128/260; 521/159; 521/174; 521/175; 521/177; 521/905; 521/914; 528/76; 528/904; 424/14; 424/16; 424/19; 424/22; 424/78

[58] Field of Search ............... 521/905, 914, 174, 175, 521/177, 159; 528/904, 76, 79; 424/78

[56] References Cited

U.S. PATENT DOCUMENTS

| 3,164,565 | 1/1965 | Calamari et al. | 528/79 |
| 3,857,932 | 12/1974 | Shepherd et al. | 424/19 |
| 3,975,350 | 8/1976 | Hudgin et al. | 521/905 |
| 3,978,266 | 8/1976 | Lock | 521/905 |

FOREIGN PATENT DOCUMENTS 2528068 1/1976 Fed. Rep. of Germany.
1135966 12/1968 United Kingdom.

Primary Examiner—H. S. Cockeram
Attorney, Agent, or Firm—Cushman, Darby & Cushman

[57] ABSTRACT

A sustained release delivery means comprising a biologically active agent and a hydrophilic linear block poly oxyalkylene- polyurethane copolymer.

10 Claims, No Drawings

DELIVERY MEANS FOR BIOLOGICALLY ACTIVE AGENTS

This application is a continuation-in-part of Ser. No. 855,332, filed Nov. 28, 1977, now U.S. Pat. No. 4,202,880, HSC Apr. 11, 1980.

This invention relates to a delivery means for a biologically active agent, and more particularly it relates to a new means for the sustained release of a biologically active agent in human beings or non-human animals.

Various sustained release means have been proposed which comprise a polymeric carrier material in combination with a biologically active agent. For example, pharmaceutical preparations have been proposed in United Kingdom Pat. No. 1,135,966 which comprise a polymeric hydrogel (obtained by copolymerising a hydrophilic mono-olefinic monomer with 0.1 to 5% of a cross linking agent) which has incorporated within it a soluble biologically active substance. In U.S. Pat. No. 3,857,932 there are proposed sustained release medicament-containing implantation dosage forms comprising a water-insoluble hydrophilic polymer selected from polymers of hydroxy lower alkyl (meth)acrylates or hydroxy lower alkoxy lower alkyl (meth)acrylates. In German Pat. No. 2,528,068 there are proposed inter alia medicament carrier systems comprising a medicament and a water-insoluble hydrophilic copolymer comprising (A) 30-90% of a hydrophilic polymer or copolymer obtained from monoolefinic monomer(s) and (B) 10-70% of a hydrophobic polymer having diolefinic terminal groups.

In U.S. Pat. No. 3,975,350 there are proposed active agent carrier, release, membrane, coating and sensing systems comprising an active agent in combination with a polyurethane polymer. More particularly, that specification discloses said systems wherein the combination is enhanced by polymers which absorb water. The main thrust of the disclosure of the specification (see, for example, column 7, lines 33 to 40 and lines 64 to 68, and the claims) is towards the use of cross-linked, and in particular thermoset, polymers. It is also indicated that the preferred diisocyanates (for use in preparing the polyurethane polymers) are aliphatic diisocyanates, and in particular methylene di(cyclohexyl isocyanate) and adiponitrile carbonate, and that aromatic diisocyanates are vastly less desirable (see column 9, lines 50–51 and 63–64).

Although the main thrust of the disclosure and claims of said U.S. Pat. No. 3,975,350 is towards cross-linked polymers, in one Example therein (Example G) there is disclosed a linear copolymer obtained from 'Carbowax' 1540, diethylene glycol and 'Hylene' W (a light stable diisocyanate having an equivalent weight of 131, produced by Du Pont). However, the polymers used according to the present invention differ from this polymer in that they are characterised by the presence of a short chain oxyalkylated diphenol as the dihydroxy component, in contrast to the diethylene glycol used in said Example G.

The said U.S. Pat. No. 3,975,350 neither teaches, nor does it render obvious to one of ordinary skill in the art, the compositions of the present invention and their properties. More particularly, that specification does not clearly disclose any block copolymers containing polyurethane regions and polyoxyalkylene regions, and its main thrust is towards polymers which are not block copolymers as so defined, and towards crosslinked polymers and therefore away from the linear non-cross-linked polymers which characterise this invention. Nor is it obvious that the compositions of this invention, which are characterised by the fact that they involve linear block copolymers, would have particularly advantageous physical properties, in particular as regards the release of biologically active agents. The compositions of the invention have the following advantages over the compositions disclosed in said U.S. Pat. No. 3,975,350:

1. They are well characterised block copolymers of high molecular weight prepared by a homogeneous one stage reaction.

2. They have unexpectedly improved mechanical properties when wet. Normally, water would plasticise the hydrophilic polymer, leading to a deterioration in properties (hence the main thrust in said U.S. Pat. No. 3,975,350 towards cross-linking, to provide a polymer with adequate properties when wet). Cross-linking is not needed with the present invention as the polymers, even though linear, are designed to have improved properties when wet.

3. Because of the lyophilic nature of the polyurethane blocks prepared using the diphenol derivative, the polymers of this invention have good solubility properties in a wider range of solvents.

4. The compatibility of the polymers of this invention with biologically active agents is better over a wider range of hydrophilicity/lipophilicity.

5. The polymers of this invention have good hydrolytic stability, even when prepared from aromatic diisocyanates, which are preferred to aliphatic diisocyanates in this invention (compare column 9, lines 60 to 64 of U.S. Pat. No. 3,975,350).

6. The polymers of this invention are easy to fabricate, and therefore there is less risk of decomposition of the biologically active agent.

The hydrophilic linear block copolymer which characterises this invention has the following advantageous properties:

(1) Because it is linear in structure, the copolymer is soluble in common organic solvents; this is important for biological applications because the copolymer can be purified, and solvent casting techniques can be used for fabrication purposes. Also, the copolymer is thermoplastic and easily moulded and extruded.

(2) It is substantially insoluble and non-erodable in body fluids.

(3) It is compatible with delicate body tissues, and causes no toxicity or related problems.

(4) The degree of hydrophilicity, and therefore of water-swellability, of the copolymer can be pre-determined by its composition. In use, the delivery means of the invention is permeated by the body fluids, which results in a diffusion path being established from the delivery means to the adjacent body tissue. As a result, there is a sustained release of the biologically active agent.

(5) It is a soft elastomer when swollen in body fluids, and therefore it can conform to body cavities and is nonirritant.

(6) A wide range of biologically active agents, as far as water solubility is concerned, can be incorporated, in solution or in suspension, in the copolymer.

According to the invention there is provide the sustained release delivery means comprising (a) a functionally effective amount of a biologically active agent, (b) a hydrophilic linear block polyoxyalkylene-polyurethane copolymer of the type ABABAB ..., substantially devoid of cross-linking, wherein A represents a hydrophilic region composed of one or more polyoxyalkylene(s) containing the repeating unit —(CH$_2$)$_2$O—, —CH$_2$CH(CH$_3$)O—, —(CH$_2$)$_3$O— and/or —(CH$_2$)$_4$O—, and B represents a hydrophobic region composed of a polyurethane obtainable in known general manner from an aromatic or aliphatic diisocyanate and a short chain oxyalkylated diphenol, optionally together with at least one alkyleneglycol of not more than 6 carbon atoms, and (c) optionally containing a biologically acceptable buffer.

The biologically active agents used according to this invention include medicaments for the curative or therapeutic treatment of human beings or non-human animals, as well as agents having desirable pharmacological properties but which do not have actual curative or therapeutic properties. An example of the latter type of agent is a contraceptive agent. Thus, included amongst the biologically active agents which are suitable for administration according to the present invention are: abortifacients, hypnotics, sedatives, tranquillisers, anti-convulsants, muscle relaxants, anti-parkinson agents, analgesics, anti-pyretic agents, anti-inflammatory agents, local anaesthetics, anti-spasmodics, anti-ulcer agents, anti-microbials, anti-malarials, hormonal agents, androgenic steroids, estrogenic and progestational steroids, sympathomimetic agents, cardiovascular agents, diuretics, anti-parasitic agents, anti-tumour agents, hypoglycaemic agents, contraceptive agents and nutritional agents. The biologically active agents used in the delivery means of this invention may be sparingly water-soluble, moderately water-soluble or very water-soluble.

The delivery means of the invention is adapted either to be positioned in a body cavity, for example the vagina, or to be implanted in body tissue, and it can be shaped by standard procedures for the intended use.

The copolymers which characterise this invention fall within the class known as amphipathic materials. A preferred polyoxyalkylene is polyoxyethylene of molecular weight 600 to 6000. The hydrophobic regions B are composed of a polyurethane which is obtainable in known general manner from a diisocyanate, for example an aromatic diisocyanate, for example 4,4'-diphenylmethane diisocyanate or toluene diisocyanate (2,4- and/or 2,6-isomers), or an aliphatic diisocyanate, for example 1,6-hexamethylene diisocyanate, isophorone diisocyanate or 4,4'-dicyclohexylmethane diisocyanate, and a short chain oxyalkylated diphenol, for example 1,1'-isopropylidene-bis-p-phenyleneoxy-di-propanol-2, optionally together with at least one alkyleneglycol of not more than 6 carbon atoms, for example ethyleneglycol, diethyleneglycol, 1,2-propyleneglycol, 1,3-butyleneglycol or 1,4-butyleneglycol. Aromatic diisocyanates are preferred over aliphatic diisocyanates.

Preferred copolymers contain 30 to 70% by weight of hydrophilic regions A and 70 to 30% by weight of hydrophobic regions B. A preferred diisocyanate is 4,4'-diphenylmethane diisocyanate, because it reacts at a convenient rate without the need for polymerisation catalysts which may be leachable and toxic. A preferred dihydroxy compound for use in block B is 1,1'-isopropylidene-bis-p-phenyleneoxy-di-propanol-2.

According to one embodiment of this invention there is provided a sustained release delivery means comprising (a) a functionally effective amount of a biologically active agent; (b) a hydrophilic linear block polyoxyalkylene-polyurethane copolymer of the type ABABAB ..., substantially devoid of cross-linking, wherein A represents a hydrophilic region composed of polyoxyethylene of molecular weight 600 to 6000, and B represents a hydrophobic region composed of a polyurethane obtainable in known general manner from an aromatic diisocyanate and a short chain oxyalkylated diphenol optionally together with at least one alkyleneglycol of not more than 6 carbon atoms, and wherein the copolymer contains 30 to 70% by weight of hydrophilic regions and 70 to 30% by weight of hydrophobic regions; and (c) optionally containing a biologically acceptable buffer.

According to another embodiment of this invention there is provided a sustained release delivery means comprising (a) a functionally effective amount of a medicament; (b) a hydrophilic linear block polyoxyalkylene-polyurethane copolymer of the type ABABAB ..., substantially devoid of cross-linking, wherein A represents a hydrophilic region composed of polyoxyethylene of molecular weight 600 to 6000, B represents a hydrophobic region composed of a polyurethane obtainable in known general manner from 4,4'-diphenylmethane diisocyanate and 1,1'-isopropylidene-bis-p-phenyleneoxy-di-propanol-2, and wherein the copolymer contains 30 to 70% by weight of hydrophilic regions and 70 to 30% by weight of hydrophobic regions, and (c) a biologically acceptable buffer.

The buffer which may optionally be present in the delivery means of the invention may be any biologically acceptable buffer, for example sodium bicarbonate or a phosphate buffer. The purpose of the buffer is to maximise the reproducibility of the effect of any particular delivery means of the invention in humans or any particular animal, where such reproducibility is desirable, by standardising the pH of the body fluids adjacent to the delivery means when it is in position in the host.

The delivery means of this invention can, for example, be obtained by first preparing the polymeric component by any standard method, and then incorporating the biologically active agent and the optional biologically acceptable buffer into the copolymer by any standard method, for example solvent casting or a compounding procedure. It is to be understood that the testing of any particular copolymer to ascertain if it is suitable for use according to this invention is a relatively simple matter which is well within the skill of the art. The amount of any particular biologically active agent which should be incorporated in a delivery means of this invention is obvious to a skilled person from his personal knowledge and/or from the relevant literature, or it is easily ascertainable by such a person without undue experimentation. Equally, the composition and amount of any buffer which may be present in a delivery means of this invention are obvious to or easily ascertainable by said skilled person.

One particularly useful embodiment of this invention consists of an intravaginal device comprising an abortifacient compound.

A suitable abortifacient compound is, for example, an abortifacient prostaglandin derivative, for example fluprostenol sodium [racemic (9S, 11R, 15R)-9,11,15-trihydroxy-16-(3-trifluoromethylphenoxy)-17,18,19,20-tetranor-5-cis, 13-trans-prostadienoic acid sodium salt]. A particularly preferred embodiment of this invention consists of an intravaginal device comprising a fluprostenol sodium, a biologically acceptable buffer, for example a phosphate buffer, and a hydrophilic copolymer obtained as described above and containing 60% by weight of polyoxyethylene of molecular weight 4000, and 40% by weight of hydrophobic polyurethane blocks obtained from approximately equal parts by weight of 4,4'-diphenylmethane diisocyanate and 1,1'-isopropylidene-bis-p-phenyleneoxy-di-propanol-2.

The rate of release in vivo of the abortifacient drug from said intravaginal device of this invention is determined by the composition of the copolymer, the size, shape and thickness of the device, the nature and amount of the abortifacient compound, and the nature and amount of any buffer, in the device. Said intravaginal device can be in the form of a disc, ring, annulus or slab, or any other shape which can be retained in the vagina.

The invention is illustrated by the following Examples:

EXAMPLE 1

(a) Preparation of copolymer—medicament mixture

Solutions of fluprostenol sodium (5 mg.) in water (0.5 ml.) and of $C^{14}$ labelled fluprostenol sodium (5 µl. having a concentration of 1 mg./ml., specific activity 133 µCi/mg.) in water were added to a solution of the elastomer described below (10 g.) in tetrahydrofuran (40 g.). The solution was cast as a film in conventional manner. The resulting film was air-dried at room temperature for 24 hours and finally dried at 70° C. in vacuo for 8 hours. The resulting polymer-medicament mixture was compression moulded at 110° C. to give a slab of 0.1 cm. thickness.

The desorption of the medicament and the radioactivity from 2 g. of the said slab into water at 37° C., using a stirring rate of 100 r.p.m., was shown to behave approximately according to the equation:

$$\frac{M_t}{M_\infty} = 4\left(\frac{Dt}{\pi l^2}\right)^{\frac{1}{2}} \text{ for } 0 \leq \frac{M_t}{M_\infty} \leq 0.6$$

where $M_t$ is the amount of medicament released by time t, is the total amount of medicament in the slab, t is the time, l is the thickness of the slab, and D is the diffusion coefficient.

The graph of $M_t/M_\infty$ against $t^{\frac{1}{2}}/1$ is a straight line, giving a value for D of ca. $5\times10^{-4}$ cm$^2$ hours$^{-1}$.

In sink conditions (i.e. where the concentration of the medicament in the medium into which it is being released in very small) in vitro the said slab (0.1 cm. thickness) releases ca. 85% of the total medicament in 4 hours, whereas with a corresponding slab of 0.17 cm. thickness this amount of release is achieved in ca. 8 hours.

(b) Preparation of copolymer

The copolymer used in preparing the abovementioned copolymer—medicament mixture was obtained as follows:

A mixture of polyethyleneglycol (600 g.; molecular weight ca. 4000) and powdered magnesium silicate (18 g.) was heated at 110° C. in vacuo for two hours. The hot mixture was filtered to give a polyol which was dry and free from alkaline residues.

4,4'-Diphenylmethane diisocyanate (91.6 g.) was melted and heated at 80° C., and to it was added a mixture of diethylene glycol (3.3 g.), 1,2-propylene glycol (2.3 g.) and 1,3-butylene glycol (2.8 g.). The resulting mixture was stirred at 80° C. for 2 hours. There was thus obtained a clear viscous diisocyanate derivative (having an isocyanate value of 23% by weight), which was used as described below.

The abovementioned polyol (80 g.) and dry 1,1'-isopropylidene-bis-p-phenyleneoxy-di-proponal-2 (34 g.) were mixed at 80° C. to give a clear solution. To this was added the abovementioned diisocyanate derivative (46 g.). The mixture was maintained at 70°–80° C. for 18 hours. The mixture was then cooled to room temperature, and post cured for 1 week at room temperature, to give a soft, flexible elastomer. This was purified by dissolution in a mixture of acetone (1500 ml.) and water (500 ml.). To this solution was added a solution of sodium carbonate (5 g.) in water (50 ml.). The resulting mixture was stirred at room temperature for 2 hours. The elastomer was precipitated by adding the polymer solution to vigorously stirred water (ca. 5 l.). The elastomer was separated by filtration, washed with water until neutral, and dried in vacuo at 80° C. for 24 hours. There was thus obtained a soft, flexible copolymer (elastomer) comprising hydrophilic polyethyleneglycol regions and hydrophobic polyurethane regions.

EXAMPLE 2

(a) Preparation of an intravaginal device

An aqueous solution of fluprostenol sodium (0.1 ml. having a concentration of 10 mg./ml.) and an aqueous solution of $C^{14}$ labelled fluprostenol sodium (5 µl. having a concentration of 1 mg./ml., specific activity 133 µCi/mg.) were added to a solution of the dried, pure copolymer prepared as described in Example 1(b) (2 g.) in tetrahydrofuran (8 g.). The mixture was homogenised by vigorous shaking. A film was cast from the mixture, allowed to dry in the air at room temperature for 24 hours, and finally at 70° C. in vacuo for 8 hours. The resulting copolymer-medicament film (0.02 g.), which contained 10 µg. of the medicament, was compression moulded at 110° C. to give a slab (dimensions: ca. 8 mm.×7 mm.×0.2 mm.). This was wrapped round a silicone tube (2.5 mm. outside diameter×10 mm.) to give an intravaginal device in the form of a medicament-containing annulus supported on a flexible core. When these devices were tested in rats (see below) they released the medicament continuously over 24 hours. The amount of medicament desorbed from the device was measured by comparing the residual radioactivity with the original radioactivity.

(b) Determination of in vivo release

Rats (Alderley Park strain, weight 250 g.), which were shown by means of a vaginal smear to be in the first day of dioestrus, were divided into 6 groups of two. The animals were treated with an intravaginal device made as described in Example 2(a).

The devices were removed from individual groups at discrete time intervals, and the residual radioactivity in the devices was measured. Comparison of this with initial levels of radioactivity showed that the medicament was desorbed from the devices in the following manner:

| Time (hours) | % Drug desorbed |
| --- | --- |
| 2 | 15–18 |
| 4 | 22–35 |
| 6 | 40–45 |
| 8 | 40–46 |
| 16 | 55–62 |

| Time (hours) | % Drug desorbed |
| --- | --- |
| 24 | 68–72 |

These results show that the drug was desorbed continuously from the devices over 24 hours when the devices were inserted into the vaginas of rats.

(c) Testing of intravaginal device in rats

Rats (Alderley Park strain, weight 250 g.), which had been mated and whose pregnancy had been confirmed by a positive sperm test on a vaginal smear, were divided into four groups on day 6 after mating. The animals (2) in the first group were untreated controls whose pregnancies were allowed to proceed normally. The animals (6) in the second group were treated with an intravaginal device made as described in Example 2(a), but containing no medicament. The animals (6) in the third group received in a single, acute, intravaginal dose of fluprostenol sodium (10 μg.) in water (0.1 ml.). The animals (8) in the fourth group were treated for 24 hours with an intravaginal device made as described in Example 2(a), after which time the devices were removed. On day 15 after mating all of the animals were sacrificed, and the number and health of the implants were assessed. The results are summarised in Table 1.

TABLE 1

| GROUPS | RAT No. | IMPLANT L* | IMPLANT R* | CONDITION OF IMPLANTS | ABORTION RATE |
| --- | --- | --- | --- | --- | --- |
| UNTREATED CONTROL | 1 | 3 | 7 | healthy | 0/2 |
|  | 2 | 1 | 7 | healthy |  |
|  | 3 | 4 | 8 | healthy |  |
| CONTROL-BLANK DEVICE | 4 | 4 | 5 | healthy |  |
|  | 5 | 4 | 6 | healthy | 0/6 |
|  | 6 | 6 | 5 | healthy |  |
|  | 7 | 9 | 7 | healthy |  |
|  | 8 | 4 | 8 | healthy |  |
|  | 9 | 6 | 4 |  |  |
| SINGLE ACUTE DOSE OF MEDICAMENT (10 μg. PER RAT) | 10 | 6 | 5 | mainly healthy | 1/6 |
|  | 11 | 4 | 4 |  |  |
|  | 12 | 6 | 7 |  |  |
|  | 13 | 7 | 2 |  |  |
| MEDICAMENT INTRAVAGINAL DEVICE (10 μg. of medicament available in each rat) | 14 | 0 | 0 |  |  |
|  | 15 | 0 | 0 |  |  |
|  | 16 | 0 | 0 |  |  |
|  | 17 | 0 | 0 |  |  |
|  | 18 | 0 | 0 |  | 8/8 |
|  | 19 | 0 | 0 |  |  |
|  | 20 | 0 | 0 |  |  |
|  | 21 | 0 | 0 |  |  |
|  | 22 | 0 | 0 |  |  |

*L stands for the left horn of the uterus
R stands for the right horn of the uterus The two groups of control animals had healthy implants, showing that the experimental procedure had had no effect on the pregnancies. The abortion rate of the rats which received a single acute dose on day 6 was much lower (abortion rate 1/6) than that of rats which were treated for 24 hours by means of the intravaginal device (abortion rate 8/8). These results indicate that sustained administration of fluprostenol sodium by means of an intravaginal device of this invention gives a superior effect to that given by a single acute vaginal dose of the same medicament.

EXAMPLE 3

(a) Preparation of an intravaginal device

Using the procedure described in Example 1(a), there was prepared a solution containing the elastomer described in Example 1(b) (8 g.), fluprostenol sodium (1 mg. in 0.1 ml. of water), and $C^{14}$ labelled fluprostenol sodium (20 μl. of an aqueous solution having a concentration of 1 mg./ml., specific activity of 133 μCi/mg.) and tetrahydrofuran (34 g.). After drying, there was obtained a polymer-medicament mixture containing 10 μg. of fluprostenol sodium per 0.08 g. of polymer.

Individual cylinders, each ca. 3 mm. diameter × 10 mm., were made by the compression moulding (at 110° C.) of 0.08 g of the polymer-medicament mixture described immediately above. When tested in vivo in rats (see below), these cylinders released 2.2–2.5 μg. of the medicament during 24 hours.

(b) Determination of in vivo release

Rats (Alderley Park strain, weight 250 g.), which were shown by means of a vaginal smear to be in dioestrus, were divided in 5 groups of two. The animals were treated with an intravaginal device made as described in Example 3(a).

The devices were removed from individual groups at discrete time intervals, and the residual radioactivity in the devices was measured. Comparison of this with initial levels of radioactivity showed that the medicament was desorbed from the devices in the following manner:

| Time (hours) | % Drug desorbed |
| --- | --- |
| 2 | 2–4 |
| 6 | 2–6 |
| 12 | 8–10 |
| 18 | 15–18 |
| 24 | 21–26 |

(c) Testing of intravaginal device in rats

Rats (Alderley Park Strain, weight 250 g.), which had been mated and whose pregnancy had been confirmed by a positive sperm test on vaginal smear, were divided into three groups on day 6 after mating. The animals (4) in the first group were controls treated with a blank intravaginal device; i.e. a device made as described in Example 3(a), but containing no medicament. The animals (6) in the second group received a single, acute, intravaginal dose of fluprostenol sodium (10 μg.) in a polycarboxylate gel ('Carbopol'; 0.1 g.). The animals (7) in the third group were each treated with an intravaginal device made as described in Example 3(a). After 24 hours these devices were removed, and a comparison of the original and residual radioactivity indicated that each rat had received 1.7–2.5 μg. of the medicament over the 24 hours. On day 15 after mating, all of the animals were sacrificed, and the number and health of the implants were assessed. The results are summarised in Table 2. These show that, whereas the incidence of abortion using a single acute vaginal dose of 10 μg. of fluprostenol sodium is 33%, a superior response (57%) is achieved using 1.7–2.5 μg. of the same medicament when administered over 24 hours by means of an intravaginal device of this invention.

TABLE 2

| Group | Rat No. | Amount Of Medicament Administered (μg.) | Implants R | Implants | Condition Of Implants | A-bortion Rate |
|---|---|---|---|---|---|---|
| Control- | 1 | 0 | 7 | 7 | Healthy | |
| Blank | 2 | 0 | 3 | 9 | Healthy | 0/4 |
| Device | 3 | 0 | 3 | 7 | Healthy | |
|  | 4 | 0 | 7 | 5 | Healthy | |
| Single | 5 | 10 | 0 | 0 | | |
| Acute | 6 | 10 | 0 | 0 | | |
| Dose of | 7 | 10 | 5 | 4 | All | |
| Medicament | 8 | 10 | 7 | 4 | unhealthy | 2/6 |
| (10 μg. | 9 | 10 | 4 | 5 | | |
| per rat) | 10 | 10 | 5 | 8 | | |
| Medicament- | 11 | 1.7 | 4 | 7 | Healthy | |
| Intravaginal | 12 | 2.5 | 0 | 0 | | |
| Device | 13 | 2.3 | 0 | 0 | | |
| (maximum | 14 | 2.3 | 0 | 0 | | |
| of 10 μg. of | 15 | not known | 0 | 0 | | 4/7 |
| medicament | | | | | | |
| per device | 16 | 2.4 | 5 | 8 | Healthy | |
| available to | | | | | | |
| each rat) | 17 | 1.7 | 7 | 6 | Healthy | |

EXAMPLE 4

(a) Preparation of intravaginal devices

Using the procedure described in Example 1(a) the following solutions were prepared using the elastomer described in Example 1(b):

(i) Elastomer (2 g.), fluprostenol sodium (1.2 mg. in 0.12 ml. of water), $C^{14}$ labelled fluprostenol sodium (5 μl. of an aqueous solution having a concentration of 1 mg./ml., specific activity 133 μCi./mg.), sodium bicarbonate (1.2 mg. in 60 μl. of water) and tetrahydrofuran (8 g.).

After drying, there was obtained a copolymer-medicament mixture containing 12 μg. of fluprostenol sodium per 0.02 g. of copolymer.

The copolymer-medicament mixture (0.02 g.) was compression moulded at 110° C. to give a slab (dimensions: ca 10 mm.×15 mm.×0.10 mm.). This was wrapped round a silicone tube (4 mm. outside diameter×15 mm.) to give an intravaginal device in the form of an annulus (dimensions: ca. 10 mm. long×4 mm. outside diameter, and having a wall thickness of 0.1 mm.) supported on a flexible core. The device contained 12 μg. of medicament.

(ii) Using the copolymer-medicament mixture (0.01 g.) described in (i) above a slab was compression moulded having dimensions: ca. 5 mm.×15 mm.×0.1 mm. This was wrapped round a silicone tube (4 mm. outside diameter×15 mm. long) to give an intravaginal device in the form of an annulus (dimensions: ca. 5 mm. long×4 mm. outside diameter, and having a wall thickness of 0.1 mm.) supported on a flexible core. The device contained 6μg. of medicament.

(iii) Using the copolymer-medicament mixture (0.005 g.) described in (i) above a slab was compression moulded having dimensions: ca. 5 mm.×8 mm.×0.1 mm. This was wrapped round a silicone tube (2.5 mm. outside diameter×15 mm. long) to give an intravaginal device in the form of an annulus (dimensions: ca. 5 mm. long×2.5 mm. outside diameter, and having a wall thickness of 0.1 mm.) supported on a flexible core. The device contained 3 μg. of medicament.

(iv) Elastomer (4 g.), fluprostenol sodium (1.2 mg. in 0.12 ml. of water), $C^{14}$ labelled fluprostenol (5 μl. of an aqueous solution having a concentration of 1 μg./ml., specific activity 133 μCi/mg.), sodium bicarbonate (1.2 mg. in 60 μl. of water) and tetrahydrofuran (16 g.) were mixed to give a solution. After drying, there was obtained a copolymer-medicament mixture containing 12 μg. of fluprostenol sodium per 0.04 g. of copolymer. The copolymer-medicament mixture (0.04 g.) was compression moulded at 110° C. to give a slab (dimensions: ca. 10 mm.×15 mm.×0.2 mm.). This was wrapped round a silicone tube (4 mm. outside diameter×15 mm.) to give an intravaginal device in the form of an annulus (dimensions: ca. 10 mm. long×4 mm. outside diameter, and having a wall thickness of 0.2 mm.) supported on a flexible core. The device contained 12 μg. of medicament.

(v) Using the copolymer-medicament mixture (0.02 g.) described in (iv) above a slab was compression moulded having dimensions: ca 5 mm.×15 mm.×0.2 mm. This was wrapped round a silicone tube (4 mm. outside diameter×15 mm.) to give an intravaginal device in the form of an annulus (dimensions: ca. 5 mm. long×4 mm. outside diameter, and having a wall thickness of 0.2 mm.) supported on a flexible core. The device contained 6 μg. of medicament.

(vi) Using the copolymer-medicament mixture (0.01 g.) described in (iv) above a slab was compression moulded having dimensions: ca 5 mm.×8 mm.×0.2 mm. This was wrapped round a silicone tube (2.5 mm. outside diameter×15 mm. long) to give an intravaginal device in the form of an annulus (dimensions: ca. 5 mm. long×2.5 mm. outside diameter, and having a wall thickness of 0.2 mm.) supported on a flexible core. The device contained 3 μg. of medicament.

(vii) Using the copolymer-medicament mixture (0.004 g.) described in (iv) above a slab was compression moulded having dimensions: ca 2 mm.×8 mm.×0.2 mm. This was wrapped round a silicone tube (2.5 mm. outside diameter×15 mm.) to give an intravaginal device in the form of an annulus (dimensions: ca 2 mm.×2.5 mm. outside diameter, and having a wall thickness of 0.2 mm.) supported on a flexible core. The device contained 1.2 μg. of medicament.

(b) Determination of in vivo release

In a series of experiments, rats (Alderley Park strain, weight 200 g.), which were shown by vaginal smear to be in the first day of dioestrus, were divided into groups of two. The animals were treated with the devices described in Example 4(a). The devices were removed from individual groups at discrete time intervals, and the residual radioactivity in the devices was measured. Comparison of this with initial levels of radioactivity showed that the medicament was desorbed from the devices in the following manner:

| For devices (i), (ii) and (iii) | |
|---|---|
| Time (hours) | % Drug desorbed |
| 2 | 25–40 |
| 5 | 40–60 |
| 8 | 72–92 |

The devices were removed at 8hr.

| For devices (iv), (v), (vi) and (vii) | |
|---|---|
| Time (hours) | % Drug descorbed |
| 4 | 21–36 |
| 8 | 36–55 |
| 16 | 65–83 |

-continued

| For devices (iv), (v), (vi) and (vii) | |
|---|---|
| Time (hours) | % Drug descorbed |
| 24 | 67–92 |

The devices were removed at 24hr.

These results show that for devices (i), (ii) and (iii) the medicament was desorbed continuously from the devices over 8 hr. when these were inserted into the vaginas of rats. For devices (iv), (v), (vi) and (vii) the medicament was desorbed continuously from the devices over 24 hrs. when these were inserted into the vaginas of rats.

(c) Testing of intravaginal devices in rats

Rats (Alderley Park strain, weight 250 g.), which had been mated and whose pregnancy had been confirmed by a positive sperm test on a vaginal smear, were divided into groups of 6 and on day 6 after mating were treated in the following way:

Group 1. Untreated; pregnancy allowed to proceed normally.

Group 2. Treated with 0.1 ml. of polycarboxylate gel ('Carbopol') containing no medicament.

Group 3. Treated with intravaginal devices prepared as described in Example 4(a) but containing no medicament.

Group 4. Treated with 0.1 ml. of polycarboxylate gel ('Carbopol') containing medicament.

Group 5. Treated with device (i), (ii) or (iii). Drug was released over 8 hr., at which time the devices were removed.

Group 6. Treated with devices (iv), (v), (vi) or (vii). Drug was released over 24 hr., at which time the devices were removed.

For animals in Groups 5 and 6 the amount of medicament administered was measured by comparing the residual radioactivity with the initial values. On day 15 after mating, all the animals were sacrificed, and the number and health of the implants were assessed. The results are summarised in table 3.

EXAMPLE 5

(a) Preparation of copolymers

Polyethyleneglycol having a molecular weight of 4000 was purified as described in Example 1. The purified, dry product had a hydroxyl value of 27.6 mg. KOHg.$^{-1}$. 1,1'-Isopropylidene-bis-p-phenyleneoxy -dipropanol-2 was purified using a procedure similar to that used for polyethyleneglycol. 4,4'-Diephenylmethane diisocyanate was distilled before use (b.p. 160–170°-L C./0.1 mm.Hg.).

Using these purified materials the following elastomers were prepared:

A. Polyethyleneglycol (51 g.) and the abovementioned bisphenol derivative (28 g.) were mixed at 80° L C., and the diisocyanate (23 g.) was added. The mixture was thoroughly mixed by stirring and then reacted at 80° C. under dry nitrogen for 36 hrs. The copolymer was cooled to room temperature and allowed to postcure for 3 days to give an elastomeric product. The elastomer contained 50% by weight of hydrophilic block and 50% by weight of hydrophobic block.

B. Polyethyleneglycol (40 g.) and the abovementioned bisphenol derivative (14.1 g.) were reacted with the diisocyanate (12.5 g.) at 80° C. in the manner described above. The resulting elastomer contained 60% by weight of hydrophilic block and 40% by weight of hydrophobic block.

C. Polyethyleneglycol (60 g.) and the abovementioned bisphenol derivative (15 g.) were reacted with the diisocyanate (15 g.) at 80° C. in the manner described above. The resulting elastomer contained 67% by weight of hydrophilic block and 33% by weight of hydrophobic block.

(b) Purification of Elastomers

Elastomers A, B and C were purified as follows:

The elastomer (50 g.) was dissolved in a mixture of absolute ethanol (400 g.) and distilled water (100 g.) at 70° C. Sodium bicarbonate (0.1 g. in 2 ml. water) was added and the mixture was stirred at 70° C. for 2 hr. The solution was added to distilled water (5 l.), causing the

TABLE 3

Rats treated on day 6 of pregnancy. Acute dosing vs. sustained release.

| Group | | Average amount drug administered (μg.) | Time of Administration (hours) | No. of rats | Abortion Rate % |
|---|---|---|---|---|---|
| 1. | Control-untreated animals | 0 | — | 6 | 0 |
| 2. | Control-blank gel (no drug) | 0 | — | 6 | 0 |
| 3. | Control-blank device (no drug) | 0 | — | 6 | 0 |
|    | 10μg. drug/0.1 ml. gel | 10 | acute | 8 | 25 |
| 4. | 5μg. drug/0.1 ml. gel | 5 | " | 8 | 38 |
|    | 2.5 μg. drug/0.1 ml. gel | 2.5 | " | 8 | 0 |
|    | 1μg. drug/0.1 ml. gel | 1 | " | 8 | 12 |
|    | 12μg. drug/0.02 g. copolymer | 10.4 | 8 | 6 | 50 |
| 5. | 6μg. drug/0.01 g. copolymer | 4.8 | 8 | 5 | 20 |
|    | 3μg. drug/0.005 g. copolymer | 2.6 | 8 | 6 | 33 |
|    | 12μg. drug/0.04 g. copolymer | 9.8 | 24 | 8 | 100 |
|    | 6μg. drug/0.02 g. copolymer | 5.0 | 24 | 10 | 90 |
| 6. | 3μg. drug/0.01 g. copolymer | 2.7 | 24 | 12 | 83 |
|    | 1.2μg. drug/0.004 g. copolymer | 1.0 | 24 | 6 | 0 |

The results show that the incidence of abortion in the pregnant rats was greater when they were treated with the sustained release devices, and that at comparable dose levels the response was increased as the duration of administration was extended.

copolymer to precipitate. The mixture was filtered and the solid residue washed with distilled water (2 l.). The solid was then stirred in distilled water (3 l.) for 24 hrs., filtered, and dried in vacuo at 80° C.

(c) Preparation of copolymer-medicament mixtures

The following procedure was carried out using each of the copolymers A, B and C:

Solutions of fluprostenol sodium (3 mg.) in water (0.3 ml.), $C^{14}$ labelled fluprostenol sodium (80 μl. having a concentration of 0.02 mg./ml., specific activity 133 μCi/mg.) in water, and sodium bicarbonate (60 μl. of a solution of 50 mg./ml.) in water, were added to a solution of the copolymer (3 g.) in tetrahydrofuran (30 ml.). The mixture was cast as film and air dried at room temperature for 24 hr. and finally at 70° C. in vacuo for 8 hr. The resulting copolymer-medicament mixture was compression moulded at 110° C. to give slabs 0.16 cm. thick.

(d) In vitro release of medicament

The desorption of the medicament and radioactivity from 0.5 g. of the said slabs was determined in the following way:

The copolymer-medicament slab (0.5 g.) was suspended from a stirrer into 500 ml. of phosphate solution buffered to pH 7 (prepared from 3.7 g. of potassium dihydrogen phosphate and 5.78 g. of disodium hydrogen orthophosphate dihydrate in 1000 ml. water) maintained at 37° C. Using a stirring rate of 100 r.p.m. the desorption of radioactivity was shown to be approximately proportional to (time)$^{\frac{1}{2}}$. Equilibrium swelling of the copolymers at 37° C. in water was:

Copolymer A ca. 100%
Copolymer B ca. 150%
Copolymer C ca. 210%

EXAMPLE 6

(a) Preparation of intravaginal devices.

The following copolymer-medicament mixtures were prepared using the elastomer described in Example 5 (copolymer A):

(i) Elastomer (3 g.), fluprostenol sodium (1.2 mg. in 0.12 ml of water), $C^{14}$ labelled fluprostenol sodium (15 μl. of an aqueous solution having a concentration of 1 mg./ml., specific activity 133 μCi/mg.), sodium bicarbonate (1.2 mg. in 60 μl. of water) and tetrahydrofuran (13 g.). After drying, there was obtained a copolymer-medicament mixture containing 12 μg. of fluprostenol sodium per 0.03 g. of copolymer.

The copolymer-medicament mixture (0.3 g.) was compression moulded at 110° C. to give a slab (dimensions: ca. 7 mm.×15 mm.×0.2 mm.). This was wrapped round a silicone tube (4 mm. outside diameter×15 mm.) to give an intravaginal device in the form of an annulus (dimensions: ca. 7 mm×4 mm. outside diameter, and having a wall thickness of 0.2 mm.) supported on a flexible core. The device contained 12 μg. of medicament.

(ii) Using the copolymer-medicament mixture (0.015 g.) described in (i) above a slab was compression moulded having the dimensions ca. 4 mm.×15 mm.×0.2 mm. This was wrapped round a silicone tube (4 mm. outside diameter×15 mm.) to give an intravaginal device in the form of an annulus (dimensions: ca. 4 mm.×4 mm. outside diameter, and having a wall thickness of 0.2 mm.) supported on a flexible core. The device contained 6 μg. of medicament.

(iii) Elastomer (1.5 g.), fluprostenol sodium (1.2 mg. in 0.12 ml. of water), $C^{14}$ labelled fluprostenol sodium (2 μl. of an aqueous solution having a concentration of 1 mg./ml., specific activity 133 μCi/mg.), sodium bicarbonate (1.2 mg. in 60 μl. of water) and tetrahydrofuran (5 g.) were mixed to give a solution. After drying, a copolymer-medicament mixture was obtained which contained 6 μg. of fluprostenol sodium per 0.0075 g. of copolymer. The copolymer-medicament mixture (0.075 g.) was compression moulded at 110° C. to give a slab (dimensions: ca 7 mm.×8 mm.×0.1 mm.). This was wrapped round a silicone tube (2.5 mm. outside diameter×15 mm. long) to give an intravaginal device in the form of an annulus (dimensions: ca. 7 mm.×2.5 mm. outside diameter, and having a wall thickness of 0.1 mm.) supported on a flexible core. In non-pregnant rats, the intravaginal devices (i) and (ii) released 70-90% of the medicament over 24 hr., whereas the intravaginal device (iii) released 70-90% in 8 hr.

(b) Testing of intravaginal devices in rats.

Rats (Alderley Park Strain, weight 250 g.), which had been mated and whose pregnancy had been confirmed by a positive sperm test on vaginal smear, were divided into groups and on day 9 after mating they were treated in the following way:

Group 1. Untreated; pregnancy allowed to proceed normally.

Group 2. Treated with 10 μg. of fluprostenol sodium in 0.05 ml. polycarboxylate ('Carbopol') gel.

Group 3. Treated with a device containing 12 μg. of medicament which is released over 24 hr.

Group 4. Treated with 5 μg. of fluprostenol sodium in 0.1 mg. of polycarboxylate ('Carbopol') gel.

Group 5. Treated with a device containing 6 μg. of medicament which is released continuously over 24 hr.

Group 6. Treated with a device containing 6 μg. of medicament which released 70-90% of medicament in 8 hr.

The devices in Groups 5 to 6 were removed after 24 hrs. and the residual radioactivity measured. Comparing this with initial values enabled the amount of drug administered to be calculated. On day 20 after mating, all the animals were sacrificed and the number and health of the implants assessed.

TABLE 4

Rats treated on day 9 of pregnancy.
Acute dosing vs. sustained release.

| Group | Average drug administered (μg.) | Time for drug release (hr.) | No. of rats | Abortion Rate % |
|---|---|---|---|---|
| 1. Control-untreated animals | 0 | | 3 | 0 |
| 2. 10μg. drug/0.05 ml. gel | 10 | acute | 6 | 67 |
| 3. 12μg. drug/0.03 g. polymer (device i) | 10.2 | 24 | 6 | 100 |
| 4. 5 μg. drug/0.1 ml. gel | 5.0 | acute | 5 | 40 |
| 5. 6μg. drug/0.015 g. polymer (device ii) | 5.0 | 24 | 5 | 100 |
| 6. 6μg. drug/0.0075 g. polymer (device iii) | 5.1 | 8 | 3 | 67 |

These results show that an extended duration of administration of the medicament results in a higher abortion rate.

EXAMPLE 7

(a) Preparation of Intravaginal Device.

The following copolymer-medicament mixtures were prepared using the elastomer described in Example 5 (copolymer A):

Elastomer (5 g.), fluprostenol sodium (12 mg. in 1.2 ml. of water), $C^{14}$ labelled fluprostenol (1 μl. of an aqueous solution having a concentration of 1 mg./ml., specific activity 133 μCi/mg.), sodium bicarbonate (12 mg. in 600 ml. of water) and tetrahydrofuran (50 g.). After drying there was obtained a copolymer-medicament mixture containing 300 μg. of fluprostenol sodium per 0.125 g. of copolymer. The copolymer-medicament mixture (0.125 g.) was compression moulded to give a slab (dimensions: ca. 15 mm×7 mm.×1 mm.). This was wrapped round a silicone tube (4 mm. outside diameter×60 mm. long) to give an intravaginal device in the form of an annulus (dimensions: ca. 7 mm.×6 mm. outside diameter, and having a wall thickness of 1 mm.) supported on a flexible core. The device contained 300 μg. of medicament.

(b) Determination of in vivo release

Beagle bitches (weight ~12-15 kg.) were treated with the intravaginal devices described in Example 6(a). The devices were removed from individual bitches at discrete time intervals, and the residual radioactivity measured. Comparison of this with initial levels of radioactivity showed that the medicament was desorbed from the devices in the following manner:

| Time (hr) | % Drug desorbed |
| --- | --- |
| 5 | 30 |
| 16 | 63 |
| 24 | 80 |

These results show that the drug was desorbed continuously from the devices over 24 hr. when the devices were inserted into the vaginas of bitches.

(c) Testing of intravaginal device in pregnant bitches.

Beagle bitches (weight 12-19 kg), which had been mated and whose pregnancy had been confirmed by palpation, were divided into 3 groups on day 25 after mating.

Group 1. These animals were treated on both day 25 and day 26 of pregnancy with annuli devices which had a wall thickness of 1 mm. and which released ca. 20-25 μg./kg. of fluprostenol sodium over 24 hr.

Group 2. These animals were treated on day 25 with annuli devices which had a wall thickness of 1 mm. and which released ca. 20-25 μg./kg. of fluprostenol sodium over 24 hr.

Group 3. These animals were treated on both day 25 and day 26 of pregnancy with annuli devices which had a wall thickness of 1 mm. and which released ca. 10 μg./kg. of fluprostenol sodium over 24 hr.

Blood samples for progesterone assay were taken from all animals in the three groups before, during and after treatment. The animals were palpated 1 week and 2 weeks after treatment to assess regression of the implants. The results are summarised in Table 5.

TABLE 5

| | | | Treatment of Pregnant Bitches with sustained release intravaginal devices. | | | | |
| --- | --- | --- | --- | --- | --- | --- | --- |
| | | | Drug Administered (μg./kg.) | | Progesterone Level | | |
| Group | Animal No. | Wt. (kg.) | day 25 | day 26 | 2 days | 7 days | Implants 2 weeks | Abortion rate % |
| 1 | 1 | 13 | 22 | 21 | basal | basal | none | |
| | 2 | 19.5 | 21 | 23 | " | " | " | 100 |
| | 3 | 13 | 20 | 22 | " | " | " | |
| | 4 | 16.5 | 19 | — | basal | recovered | present | |
| 2 | 5 | 13 | 22 | — | " | recovered | " | 0 |
| | 6 | 11.5 | 25 | — | " | recov- | | |

TABLE 5-continued

| | | | Treatment of Pregnant Bitches with sustained release intravaginal devices. | | | | |
| --- | --- | --- | --- | --- | --- | --- | --- |
| | | | Drug Administered (μg./kg.) | | Progesterone Level | | |
| Group | Animal No. | Wt. (kg.) | day 25 | day 26 | 2 days | 7 days | Implants 2 weeks | Abortion rate % |
| | | | | | | ered | | |
| | 7 | 14.4 | 7 | 7 | basal | basal | none | |
| 3 | 8 | 12.2 | 11 | 9 | " | " | " | 66 |
| | 9 | 15.7 | 11 | 11 | basal | near basal | present | |

A comparison of the incidence of abortion in Groups 1 to 3 shows that the duration of administration is an important feature of the treatment and that administration of the medicament over 48 hours gives a better abortion rate as compared to that obtained when treatment is given over 24 hrs.

EXAMPLE 8

The bitches in Example 7 which failed to abort were treated with sustained release intravaginal devices containing fluprostenol sodium. The animals were treated on day 57 of pregnancy with annuli devices described in Example 7. These devices were designed to release 20 to 25 μg./kg. of medicament over 24 hr. when inserted into the vagina of the pregnant bitches. The devices were removed after 24 hr. The results are summarised in Table 6.

TABLE 6

| Induction of parturition in pregnant bitches. | | | | | |
| --- | --- | --- | --- | --- | --- |
| Animal (No.) | Wt. (kg.) | Drug Administered (μg.) | Day of Treatment | Day of Whelping | Expected day of Whelping |
| 4 | 19 | 493 | 57 | 58 | 62-64 |
| 5 | 16 | 384 | " | 58 | " |
| 9 | 20 | 342 | " | 60 | " |
| 6 | 12.5 | 242 | " | 59 | " |

In all cases parturition was induced, and all of the bitches gave birth to live healthy pups.

EXAMPLE 9

(a) Preparation of copolymer-medicament mixture

Copolymer (B, as described in Example 5, 3.6 g.), fluprostenol sodium (10 mg., i.e. 2 ml. of a 5 mg./ml. solution) in water, $C^{14}$ labelled fluprostenol sodium (5 μl. of a 0.02 mg./ml. solution in water, specific activity 133 μCi/mg.), and 200 μl. of buffer solution (pH 7: a solution of 3.9 g. of potassium dihydrogen orthophosphate and 6.1 g. of disodium hydrogen orthophosphate dihydrate in 100 ml. of distilled water), were dissolved in a mixture of absolute ethanol (18 ml.) and distilled water (3.6 ml.) at 70° C. The solution was cast as a film which was air dried at room temperature for 18 hr. and then finally in vacuo at 80°/8 hr.

(b) Evaluation of in vivo release

The copolymer-medicament mixture was compression moulded at 110° C. to give a slab (0.16 cm. thick), and discs (weighing ca. 0.145 g.) were cut from the slab. The use of these discs as sustained release intravaginal devices was tested in non-pregnant bitches.

Animals were separated into 4 groups of two, and the devices were placed high in the vaginal vault of the animals. At 1, 2, 5 and 8 hrs. the device were removed and the residual radioactivity measured. A comparison of this with the original values showed that the devices released medicament continuously over 8 hr. The results are summarised below:

| Time (hours) | % Drug desorbed from device |
| --- | --- |
| 1 | 23–28 |
| 2 | 44–49 |
| 5 | 58–64 |
| 8 | 65–80 |

The incorporation of buffer in the device maintained the pH of the vagina at 6–7 during the release period and ensured reproducibility of the release of the medicament.

EXAMPLE 10

These hydrophilic copolymers will also act as drug releasing carriers for medicaments having very low water solubility This can be demonstrated using progesterone.

(a) Preparation of copolymer-medicament mixture.

Progesterone (10 mg.), 1$\mu$Ci of $C^{14}$ labelled progesterone (60.7 $\mu$Ci/m.mol. in 530 $\mu$l. benzene), and the copolymer (Example 5, copolymer B; 1g.) were dissolved in tetrahydrofuran (10 ml.). The solution was air dried for 18 hr. at room temperature and finally at 80° C. in vacuo for 8 hr. The resulting copolymer-medicament mixture was moulded at 110° C. to give a film 0.02 cm. thick.

(b) In vitro release of medicament.

0.2 g. of the film was supported from the end of a stirrer into 500 ml. of distilled water at 37° C. The stirring rate was 150 r.p.m. The desorption of the medicament with time was estimated by measuring the radioactivity in the distilled water. After 24 hr. the swollen film was dissolved in tetrahydrofuran and the residual radioactivity measured. The desorption of medicament with time is summarised below:

| Time (hr.) | % Progesterone desorbed |
| --- | --- |
| 1 | 8 |
| 2 | 13 |
| 3 | 18 |
| 9 | 24 |
| 17 | 33 |
| 24 | 34 |

The desorption of the progesterone from the device was determined by the polymeric carrier and also by the low solubility of progesterone in distilled water. If the distilled water was continuously changed to maintain "sink conditions", then approximately complete release of the progesterone was achieved.

EXAMPLE 11

This Example illustrates further the use of a hydrophilic copolymer as a drug releasing carrier for a medicament of low water solubility [tamoxifen citrate, i.e. 1-(p-$\beta$-dimethylaminoethoxyphenyl)-1,2-trans-diphenylbut-1-ene citrate].

(a) Preparation of copolymer-medicament mixture.

$C^{14}$ labelled tamoxifen citrate (10 mg.; specific activity 0.33 $\mu$Ci/mg.) and copolymer (Example 5, copolymer B; 1 g.) were dissolved in tetrahydrofuran (10 ml.). The solution was air dried at room temperature for 18 hr. and finally at 80° C. in vacuo for 8 hr. The copolymer-medicament mixture was moulded at 110° C. to give a film 0.02 cm. thick.

(b) In vitro release of medicament

Using the procedure described in Example 10(b) but using the tamoxifen citrate-copolymer mixture the following results were obtained for desorption of the medicament:

| Time (hr) | % desorbed |
| --- | --- |
| 0.1 | 6 |
| 0.2 | 16 |
| 0.5 | 23 |
| 1 | 34 |
| 3 | 39 |
| 17 | 42 |
| 72 | 50 |

This illustrates that tamoxifen citrate, which is sparingly soluble in water, can be released in a sustained fashion from the abovemention copolymer.

What we claim is:

1. The sustained release delivery means comprising:
    (a) a functionally effective amount of a biologically active agent; and
    (b) a hydrophilic linear block polyoxyalkylene-polyurethane copolymer of the type ABABAB . . . having blocks A linked to blocks B, substantially devoid of cross-linking, wherein A represents a hydrophilic block comprising one or more polyoxyalkylene moieties of molecular weight 600 to 6000, and B represents a hydrophobic block comprising a polyurethane moiety obtainable by reacting an aromatic or aliphatic diisocyanate with a short chain oxyalkylated diphenol.

2. A sustained release delivery means as claimed in claim 1 wherein B represents a hydrophobic block comprising a polyurethane moiety obtainable by reacting an aromatic or aliphatic dissocyanate with a short chain oxyalkylated diphenol and at least one alkyleneglycol of not more than 6 carbon atoms.

3. A sustained release delivery means as claimed in claim 1 wherein A represents a hydrophilic block comprising polyoxyethylene of molecular weight 600 to 6000.

4. A sustained release delivery means as claimed in claim 1 wherein the short chain oxyalkylated diphenol is 1,1'-isopropylidene-bis-p-phenyleneoxy-dipropanol-2.

5. A sustained release delivery means as claimed in claim 1 which contains a biologically acceptable buffer.

6. A sustained release delivery means as claimed in claim 2 which contains a biologically acceptable buffer.

7. The sustained release delivery means comprising:
    (a) a functionally effective amount of a biologically active agent; and
    (b) a hydrophilic linear block polyoxyalkylene—polyurethane copolymer substantially devoid of cross-linking and comprising the reaction product of (1) an aromatic or aliphatic diisocyanate, (2) at least one polyoxyalkylene of molecular weight 600 to 6000, and (3) a short chain oxyalkylated diphenol.

8. A sustained release delivery means as claimed in claim 7 wherein said block copolymer (b) comprises the reaction product of (1) an aromatic or aliphatic diisocyanate, (2) at least one polyoxyalkylene of molecular weight 600 to 6000, (3) a short chain oxyalkylated diphenol, and (4) at least one alkyleneglycol of not more than 6 carbon atoms.

9. A sustained release delivery means as claimed in claim 7 which contains a biologically acceptable buffer.

10. A sustained release delivery means as claimed in claim 8 which contains a biologically acceptable buffer.

* * * * *